United States Patent
Klausmeyer et al.

(10) Patent No.: US 10,562,832 B2
(45) Date of Patent: *Feb. 18, 2020

(54) METHOD FOR MAKING 1,1,3,3-TETRACHLOROPROPENE

(71) Applicant: OCCIDENTAL CHEMICAL CORPORATION, Dallas, TX (US)

(72) Inventors: Rodney L. Klausmeyer, Wichita, KS (US); Darrell G. Hollis, Conway Springs, KS (US); Keith S. Kramer, Andover, KS (US); John L. Dawkins, Derby, KS (US); Derrek Rae Burrows, Wichita, KS (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,796

(22) Filed: May 2, 2018

(65) Prior Publication Data
US 2018/0251415 A1     Sep. 6, 2018

Related U.S. Application Data

(63) Continuation of application No. 15/311,570, filed as application No. PCT/US2015/030800 on May 14, 2015, now Pat. No. 9,969,664.

(60) Provisional application No. 61/994,323, filed on May 16, 2014.

(51) Int. Cl.
C07C 17/25       (2006.01)
C07C 17/383     (2006.01)

(52) U.S. Cl.
CPC ............. *C07C 17/25* (2013.01); *C07C 17/383* (2013.01); *Y02P 20/127* (2015.11)

(58) Field of Classification Search
CPC ........ C07C 17/25; C07C 17/383; C07C 21/04; Y02P 20/127
See application file for complete search history.

(56) References Cited

U.S. PATENT DOCUMENTS

| | | |
|---|---|---|
| 3,637,872 A | 1/1972 | Berkowitz |
| 8,115,038 B2 | 2/2012 | Wilson et al. |
| 2003/0028057 A1 | 2/2003 | Owens et al. |
| 2008/0154072 A1 | 6/2008 | Owens et al. |
| 2013/0035526 A1 | 2/2013 | Elsheikh et al. |
| 2013/0053374 A1 | 2/2013 | Inoue et al. |
| 2014/0171698 A1 | 6/2014 | Elsheikh et al. |
| 2014/0221705 A1 | 8/2014 | Wang et al. |

FOREIGN PATENT DOCUMENTS

| | | |
|---|---|---|
| CN | 101903312 A | 12/2010 |
| CN | 102858725 A | 1/2013 |
| JP | 2011057650 | 3/2011 |

OTHER PUBLICATIONS

International Search Report and Written Opinion for Appl. No. PCT/US2015/030800 dated Aug. 13, 2015, pp. 1-10.
Office Action from Japanese Patent Office in Japanese Application No. 2017-512861; dated Apr. 2, 2019; English translation provided, dated Apr. 16, 2019.

*Primary Examiner* — Jafar F Parsa
(74) *Attorney, Agent, or Firm* — Renner, Kenner; Arthur M. Reginelli

(57) ABSTRACT

A process for the manufacture of 1,1,3,3-tetrachloropropene, the process comprising dehydrochlorinating 1,1,1,3,3-pentachloropropane.

13 Claims, 5 Drawing Sheets

METHOD FOR MAKING 1,1,3,3-TETRACHLOROPROPENE

This application is a continuation application of U.S. Non-Provisional application Ser. No. 15/311,570 filed on Nov. 16, 2016, which is a U.S. National-Stage Application of PCT/US2015/030800 filed on May 14, 2015, and claims the benefit of U.S. Provisional Patent Application Ser. No. 61/994,323 filed on May 16, 2014, which are incorporated herein by reference.

FIELD OF THE INVENTION

Embodiments of the present invention relate to methods for manufacturing 1,1,3,3-tetrachloropropene from 1,1,1,3,3-pentachloropropane.

BACKGROUND OF THE INVENTION

U.S. Pat. No. 6,313,360 teaches a process for the manufacture of 1,1,1,3,3-pentachloropropane by reacting carbon tetrachloride and vinyl chloride in the presence of a catalyst mixture comprising organophosphate solvent, iron metal, and ferric chloride under conditions sufficient to produce the 1,1,1,3,3-pentachloropropane. The resultant 1,1,1,3,3-pentachloropropane is contained within a product mixture that is first separated within, for example, a flash tower to remove ferric chloride, organophosphates, and other high boiling components. This flash tower can be operated at temperatures below 116° C. and from about 0.02 to 0.07 atmospheres. The distillate fraction is then further purified using two or more distillation towers that may be operated under partial vacuum at temperatures preferably less than 138° C. The production of 1,1,1,3,3-pentachloropropane is likewise disclosed in U.S. Pat. No. 6,187,978.

SUMMARY OF THE INVENTION

Figure 1:
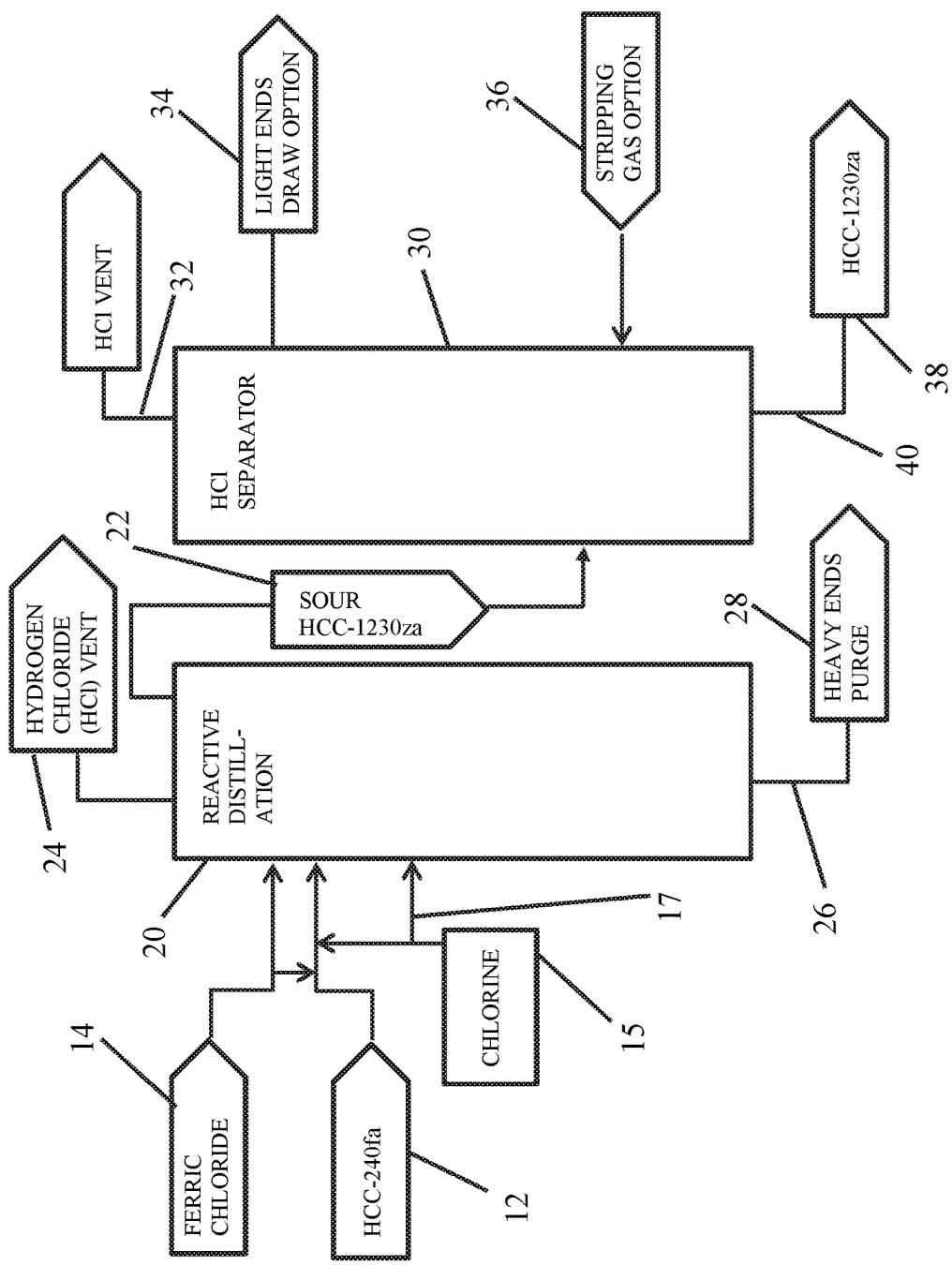
FIG. 1 is a flow chart diagram of a process for producing 1,1,3,3-tetrachloropropene according to embodiments of the invention wherein a purified stream of 1,1,1,3,3-pentachloropropane is reactively distilled.

Embodiments of the present invention provide a process for the manufacture of 1,1,3,3-tetrachloropropene, the process comprising dehydro chlorinating 1,1,1,3,3-pentachloropropane.

DETAILED DESCRIPTION OF ILLUSTRATIVE EMBODIMENTS

Embodiments of the invention are based, at least in part, on the discovery of a process for producing 1,1,3,3-tetrachloropropene (HCC-1230za) by dehydrochlorinating 1,1,1,3,3-pentachloropropane (HCC-240fa) in the presence of a Lewis acid and optionally an oxidizing agent. In one or more embodiments, the 1,1,3,3-tetrachloropropene is continuously produced and removed from the dehydrochlorination vessel, along with one or more byproducts, by employing reactive distillation techniques. In certain advantageous embodiments, the 1,1,1,3,3-pentachloropropane is contained within a crude 1,1,1,3,3-pentachloropropane stream that may include carbon tetrachloride.

Process for Producing 1,1,1,3,3-Pentachloropropane

In one or more embodiments, 1,1,1,3,3-pentachloropropane may be produced by the use of known methods. In this regard, U.S. Pat. Nos. 6,313,360 and 6,187,978 are incorporated herein by reference. In one or more embodiments, the 1,1,1,3,3-pentachloropropane is produced by reacting carbon tetrachloride and vinyl chloride in the presence of a catalyst mixture comprising organophosphate solvent (e.g., tributylphosphate), iron metal, and ferric chloride under conditions sufficient to produce 1,1,1,3,3-pentachloropropane.

Isolation of 1,1,1,3,3-Pentachloropropane Stream from Raw Product Stream

In one or more embodiments, a raw 1,1,1,3,3-pentachloropropane stream, which is produced by the reaction defined above, may be purified or partially purified by employing known techniques, such as those disclosed in U.S. Pat. No. 6,313,360, which is incorporated herein by reference. In one or more embodiments, a raw 1,1,1,3,3-pentachloropropane stream is prepared by reacting carbon tetrachloride with vinyl chloride in the presence of organophosphate solvent, iron metal, and/or ferric chloride as described above. This raw 1,1,1,3,3-pentachloropropane stream may then undergo a first separation wherein ferric chloride, amines, nitriles, amides, and/or phosphates, as well as other high boiling components, are separated from a distillate fraction that may include carbon tetrachloride, vinyl chloride, and 1,1,1,3,3-pentachloropropane, as well as other light byproducts such as various chlorinated compounds such as chloroform and chlorobutane. In one or more embodiments, this first separation step produces a crude 1,1,1,3,3-pentachloropropane stream, which will be described in greater detail below.

In one or more embodiments, this first separation step may take place at a temperature from about 70° C. to about 120° C., or in other embodiments from about 80° C. to about 90° C.

In one or more embodiments, this first separation step may take place at a pressure of at least 0.020 atmospheres, in other embodiments at least 0.025 atmospheres, and in other embodiments at least 0.030 atmospheres. In these or other embodiments, this first separation step may take place at pressures of at most 0.07 atmospheres, in other embodiments at most 0.05 atmospheres, and in other embodiments at most 0.04 atmospheres. In particular embodiments, this first separation step may take place at pressures from about 0.02 atmospheres to about 0.07 atmospheres, or in other embodiments from about 0.025 atmospheres to about 0.040 atmospheres.

Where further purification of the 1,1,1,3,3-pentachloropropane stream is desired, a second separation step may be performed. According to this second separation step, the distillate fraction from the first separation step (i.e., the 1,1,1,3,3-pentachloropropane stream), which may contain unconverted vinyl chloride, unconverted carbon tetrachloride, and other light byproducts, is further separated to isolate the 1,1,1,3,3-pentachloropropane and its isomers. In one or more embodiments, the second purification step includes a second distillation to produce a partially purified 1,1,1,3,3-pentachloropropane stream.

In one or more embodiments, this second separation step may take place at a temperature of from about 60° C. to about 160° C., or in embodiments from about 70° C. to about 130° C.

In one or more embodiments, this second separation step may take place at a pressure of at least 0.05 atmospheres, in other embodiments at least 0.10 atmospheres, and in other embodiments at least 0.20 atmospheres. In these or other embodiments, this first separation step may take place at pressures of at most 0.50 atmospheres, in other embodiments at most 0.40 atmospheres, and in other embodiments at most 0.30 atmospheres. In particular embodiments, this first separation step may take place at pressures from about 0.05 atmospheres to about 0.50 atmospheres, or in other embodiments from about 0.10 atmospheres to about 0.30 atmospheres.

Characteristics of 1,1,1,3,3-Pentachloropropane Stream

The 1,1,1,3,3-pentachloropropane used in the process of this invention may be prepared as described above. In one or more embodiments, the 1,1,1,3,3-pentachloropropane is contained within a 1,1,1,3,3-pentachloropropane stream, which includes the 1,1,1,3,3-pentachloropropane and one or more optional constituents.

In one or more embodiments, the 1,1,1,3,3-pentachloropropane stream is a purified 1,1,1,3,3-pentachloropropane stream that is at least substantially devoid of other chemical constituents. As used herein, substantially devoid refers to that amount or less of other chemical constituents that would otherwise have a deleterious impact on the practice of one or more aspects of the invention. In one or more embodiments, the purified 1,1,1,3,3-pentachloropropane stream is substantially devoid of carbon tetrachloride, vinyl chloride, chlorobutane, chloroform, pentachloropropane isomers other than 1,1,1,3,3-pentachloropropane (e.g. 1,1,1,2,3-pentachloropropane), iron and/or iron compounds, amines, nitriles, amides, and phosphates. In one or more embodiments, the purified 1,1,1,3,3-pentachloropropane stream includes less than 5,000 ppm (i.e. 0.5 wt %), in other embodiments less than 1000 ppm, and in other embodiments less than 500 ppm 1,1,1,2,3-pentachloropropane based on the entire weight of the stream. In one or more embodiments, the purified 1,1,1,3,3-pentachloropropane steam includes less than 10,000 ppm (i.e. 1 wt %), in other embodiments less than 500 ppm, and in other embodiments less than 100 ppm carbon tetrachloride based upon the entire weight of the stream. In these or other embodiments, the partially purified 1,1,1,3,3-pentachloropropane steam includes less than 100 ppm, in other embodiments less than 10 ppm, and in other embodiments less than 5 ppm iron and/or iron compounds, amines, nitriles, amides, and phosphates.

In other embodiments, the 1,1,1,3,3-pentachloropropane stream employed in the practice of this invention is a partially purified 1,1,1,3,3-pentachloropropane stream, which refers to a stream that is substantially devoid of compounds other than pentachloropropanes. In one or more embodiments, the partially purified steam may include at most 2.0 wt % pentachloropropanes other than 1,1,1,3,3-pentachloropropane (i.e. other pentachloropropane isomers) including, but not limited to, 1,1,1,2,3-pentachloropropane. In one or more embodiments, the partially purified 1,1,1,3, 3-pentachloropropane steam is substantially devoid of carbon tetrachloride, vinyl chloride, iron and/or iron compounds, amines, nitriles, amides, and phosphates. In particular embodiments, the partially purified 1,1,1,3,3-pentachloropropane steam includes less than 10,000 ppm (i.e. 1 wt %), in other embodiments less than 500 ppm, and in other embodiments less than 100 ppm carbon tetrachloride. In these or other embodiments, the partially purified 1,1,1,3,3-pentachloropropane steam includes less than 100 ppm, in other embodiments less than 10 ppm, and in other embodiments less than 5 ppm iron and/or iron compounds, amines, nitriles, amides, and phosphates.

In yet other embodiments, the 1,1,1,3,3-pentachloropropane stream is a crude 1,1,1,3,3-pentachloropropane stream that is delivered directly from one or more of the processes described above for the synthesis of 1,1,1,3,3-pentachloropropane. In one or more embodiments, the crude 1,1,1,3,3-pentachloropropane steam is substantially devoid of iron and/or iron compounds, amines, nitriles, amides, and phosphates. In one or more embodiments, the crude 1,1,1,3,3-pentachloropropane steam includes less than 100 ppm, in other embodiments less than 10 ppm, and in other embodiments less than 5 ppm iron and/or iron compounds, amines, nitriles, amides, and phosphates. In one or more embodiments, the crude 1,1,1,3,3-pentachloropropane steam includes carbon tetrachloride. In one or more embodiments, the crude 1,1,1,3,3-pentachloropropane steam includes from about 10 wt % to about 70 wt %, in other embodiments from about 20 wt % to about 60 wt %, and in other embodiments from about 30 wt % to about 50 wt % carbon tetrachloride based upon the entire weight of the stream. In one or more embodiments, the crude 1,1,1,3,3-pentachloropropane stream includes one or more chlorinated compounds selected from vinyl chloride, chlorobutane, and chloroform. In one or more embodiments, the crude 1,1,1,3,3-pentachloropropane steam includes from about 0.1 wt % to about 10 wt %, in other embodiments up to about 6 wt %, and in other embodiments up to about 5 wt % of one or more chlorinated compounds selected from vinyl chloride, chlorobutane, chloroform, and combinations thereof, based upon the entire weight of the stream.

Process for Producing 1,1,3,3-Tetrachloropropene

As indicated above, 1,1,3,3-tetrachloropropene may be formed by dehydrochlorinating 1,1,1,3,3-pentachloropropane in the presence of a Lewis acid and optionally an oxidizing agent. Exemplary Lewis acids include halides of metals and semimetals, such as aluminum, titanium, tin, antimony, and iron halides. In particular embodiments, ferric chloride is employed as the Lewis acid. The Lewis acid can be added either dry or as a slurry. Exemplary oxidizing agents include various chlorides including chlorine and sulfuryl chloride. In particular embodiments, chlorine is used as the oxidizing agent. For ease of description, specific embodiments of this invention may be described with respect to ferric chloride and chlorine, and the skilled artisan will be able to readily extend practice of these embodiments to other Lewis acids and oxidizing agents. Hydrogen chloride may be produced as a byproduct. The ferric chloride may be introduced to the 1,1,1,3,3-pentachloropropane stream prior to or during the dehydrochlorination reaction.

Where the dehydrochlorination reaction is conducted within a reaction vessel, the ferric chloride may be separately and individually added to the reaction vessel continuously during the course of the reaction or periodically during the course of the reaction. For example, ferric chloride may be fed into the reaction vessel once per 0.5 to 3 liquid turnovers, wherein one turnover is the time calculated as the ratio of liquid inventory in the reaction vessel to the liquid flow rate out of the reaction vessel.

In one or more embodiments, the amount of ferric chloride present during the dehydrochlorination reaction is a catalytic amount, which refers to that amount that promotes dehydrochlorination reaction. In one or more embodiments, the amount of ferric chloride present during the dehydrochlorination reaction may be at least 30 ppm, in other embodiments at least 100 ppm, and in other embodiments at least 200 ppm, based upon the weight of the reaction mixture, which includes all constituents within the bottom of the distillation column. In these or other embodiments, the amount of ferric chloride present during the dehydrochlorination reaction may be at most 10,000 ppm, in other embodiments at most 5000 ppm, and in other embodiments at most 3000 ppm, based upon the weight of the reaction mixture. In one or more embodiments, the amount of ferric chloride present during the dehydrochlorination reaction is from about 30 to about 10,000 ppm, in other embodiments from about 100 to about 5000 ppm, and in other embodiments from about 200 to about 3000 ppm, based upon the weight of the reaction mixture.

In one or more embodiments, where an oxidizing agent, such as chlorine, is present during the dehydrochlorination reaction, the amount of oxidizing agent may be from about 100 ppm to about 3 wt %, or in other embodiments from about 1,000 ppm to about 10,000 ppm.

A process for the preparation of 1,1,3,3-tetrachloropropene may include reactive distillation, which includes dehydrochlorinating 1,1,1,3,3-pentachloropropane in a reaction zone in the presence of ferric chloride to produce 1,1,3,3-tetrachloropropene and hydrogen chloride while removing the 1,1,3,3-tetrachloropropene and hydrogen chloride from the reaction zone by distillation during the course of the reaction. In one or more embodiments, the 1,1,3,3-tetrachloropropene and hydrogen chloride are removed continuously during the course of the reaction. In one or more embodiments, the 1,1,1,3,3-pentachloropropane is fed continuously into the reactive distillation system. The reactive distillation system may be operated in a continuous process wherein the 1,1,1,3,3-pentachloropropane stream addition and the 1,1,3,3-tetrachloropropene product removal, as well as the removal of hydrogen chloride byproduct, are performed at the same time.

In one or more embodiments, the reactive distillation system may include a reaction zone, a separation zone, and a condensing zone. The 1,1,1,3,3-pentachloropropane stream enters the reaction zone, which is generally located below the separation zone. The liquid in the reaction zone is heated and agitated. Practice of the present invention is not limited by the process or mechanism for providing agitation and heat. For example, the agitation can be provided via pumped circulation loops or by stirring. Heat can be provided through a jacket on the vessel, or by internal heat exchangers, or by external heat exchangers.

In one or more embodiments, the 1,1,1,3,3-pentachloropropane stream does not contain more than 1,000 ppm water.

In one or more embodiments, the reactive distillation step may take place at temperatures greater than 20° C., in other embodiments greater than 30° C., in other embodiments greater than 40° C., and in other embodiments greater than 50° C. In one or more embodiments, reactive distillation may take place at a temperature of from about 60° C. to about 160° C., or in other embodiments from about 80° C. to about 100° C.

In one or more embodiments, the reactive distillation step may take place at pressures of at least 0.05 atmospheres, in other embodiments at least 0.10 atmospheres, and in other embodiments at least 0.20 atmospheres. In these or other embodiments, this first separation step may take place at pressures of at most 0.50 atmospheres, in other embodiments at most 0.40 atmospheres, and in other embodiments at most 0.30 atmospheres. In particular embodiments, this first separation step may take place at pressures from about 0.05 atmospheres to about 0.50 atmospheres, or in other embodiments from about 0.10 atmospheres to about 0.40 atmospheres.

Process for Producing 1,1,3,3-Tetrachloropropene Using Reactive Distillation

An exemplary process for preparing 1,1,3,3-tetrachloropropene from a purified 1,1,1,3,3-pentachloropropane stream is shown in FIG. 1. The process includes providing a purified 1,1,1,3,3-pentachloropropane stream 12 and a ferric chloride source 14, and delivering the same to a reactive distillation column 20, wherein 1,1,1,3,3-pentachloropropane is distilled under appropriate heat and pressure to form a condensate fraction 22, which may include both 1,1,3,3-tetrachloropropene and hydrogen chloride, as well as other volatile byproducts.

The reactive distillation step selectively dehydrochlorinates 1,1,1,3,3-pentachloropropane to make hydrogen chloride (HCl) and 1,1,3,3-tetrachloropropene, where 1,1,3,3-tetrachloropropene and hydrogen chloride are distilled overhead. As suggested above, this reactive distillation may take place at temperatures from about 60° C. to about 160° C. and pressures from about 0.05 atmospheres to about 0.5 atmospheres. As also suggested above, ferric chloride 14 can be added to the purified 1,1,1,3,3-pentachloropropane stream 12 before purified 1,1,1,3,3-pentachloropropane stream 12 is introduced to reactive distillation column 20. In other embodiments, ferric chloride 14 can be introduced to purified 1,1,1,3,3-pentachloropropane stream 12 within reactive distillation column 20.

In one or more embodiments, an oxidizing agent 15, such as chlorine, is introduced to reactive distillation column 20. This oxidizing agent 15 may be introduced to the feed line introducing 1,1,1,3,3-pentachloropropane stream 12, or a feed line 17 that directly introduces oxidizing agent 15 to reactive distillation column 20.

A volatiles fraction 24, which primarily includes hydrogen chloride, may be collected from distillation column 20 and vented.

The bottom fraction 26 from reactive distillation column 20 can be routed to heavy ends purge 28.

Condensate fraction 22, which may also be referred to as sour 1,1,3,3-tetrachloropropene fraction 22 or condensation fraction 22, is rich in 1,1,3,3-tetrachloropropene, and contains hydrogen chloride. Condensate fraction 22 may be further purified by removal of hydrogen chloride within a hydrogen chloride separator 30. In one or more embodiments, hydrogen chloride separator 30 may include a stripping tower. In other embodiments, separator 30 may include a distillation column.

Volatiles fraction 32, which primarily includes hydrogen chloride, may be vented from separator 30 or recovered overhead. Other light compounds which have a boiling point below that of the desired 1,1,3,3-tetrachloropropene, may be collected as a distillate fraction 34, which may be drawn by a top section side draw at or near the top section of a distillation tower used as hydrogen chloride separator 30. Distillate fraction 34 may also be referred to as light ends draw 34.

In one or more embodiments, a stripping gas 36 may be introduced into separator 30 where separator 30 is a stripping tower.

The desired 1,1,3,3-tetrachloropropene product 38 may be recovered via a bottom section or a lower side draw 40 of a distillation tower, where a distillation tower is used as separator 30. Where separator 30 is a distillation tower, the distillation may take place at temperatures from about 60° C., to about 160° C., and pressures from about 0.03 atmospheres to about 1.1 atmospheres.

In one or more embodiments, desired 1,1,3,3-tetrachloropropene product 38 can be further purified by using, for example, additional distillation techniques to provide a product of desired purity.

Figure 2:
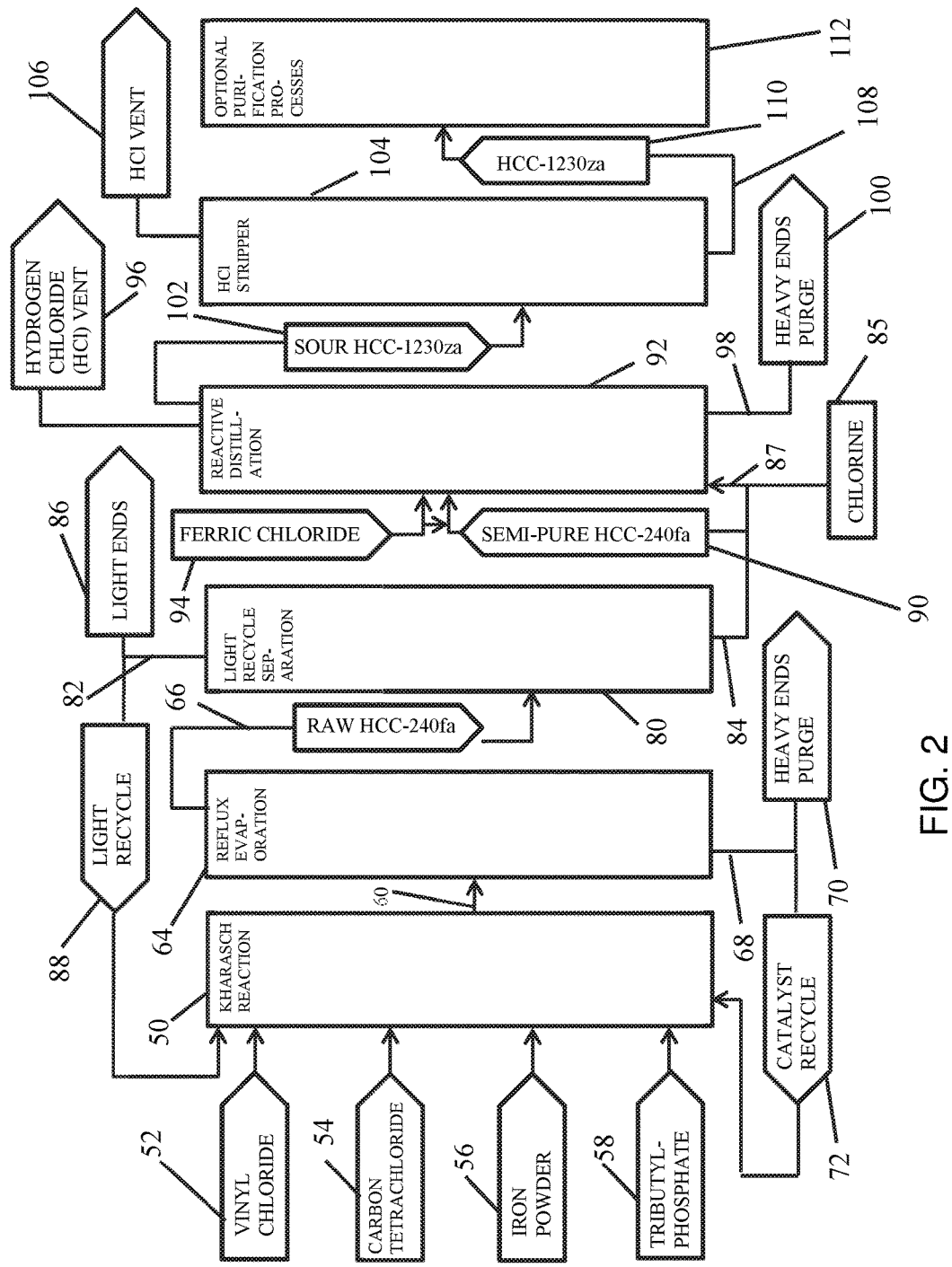
FIG. 2 is a flow chart diagram of a process for producing 1,1,3,3-tetrachloropropene according to embodiments of the invention wherein a partially purified stream of 1,1,1,3,3-pentachloropropane is reactively distilled.

Process for Producing 1,1,3,3-Tetrachloropropene Using Partially Purified Stream An exemplary process for producing 1,1,3,3-tetrachloropropene from a partially purified 1,1,1,3,3-pentachloropropane stream is show in FIG. 2. To begin with, 1,1,1,3,3-pentachloropropane is prepared within a reaction vessel 50 by combining vinyl chloride 52, carbon tetrachloride 54, iron powder 56, and an organophosphate (e.g., tributylphosphate) 58. As is generally known in the art, the reaction taking place within a reactor 50, which may be referred to as the Kharasch reaction, takes place at temperatures of from about 80° C. to about 125° C. The Kharasch reaction combines vinyl chloride and carbon tetrachloride (CTC) to make 1,1,1,3,3-pentachloropropane. As is also known in the art, where excess carbon tetrachloride is supplied to reactor 50, reaction selectivity can be improved thereby producing fewer heavy ends.

The crude 1,1,1,3,3-pentachloropropane product stream 60 exits reactor 50 and is delivered to a reflux evaporator 64, wherein the 1,1,1,3,3-pentachloropropane and light ends are separated as an overhead fraction 66 from the other components, which can include heavy ends and catalyst components. The other components, which have a higher boiling point and include, for example, organophosphates, are separated as a heavy ends fraction 68. In particular embodiments, heavy ends fraction 68 can be routed to heavy ends purge 70 or, depending on the nature of heavy ends 68, provided as a catalyst recycle stream 72 to reactor 50. In one or more embodiments, reflux evaporator 64 may be operated at temperatures of from about 70° C. to about 120° C., and pressures of from about 0.02 atmospheres to about 0.07 atmospheres.

Overhead fraction 66, which may also be referred to as raw 1,1,1,3,3-pentachloropropane product stream 66, crude 1,1,1,3,3-pentachloropropane product stream 66, or distillate stream 66, contains unconverted carbon tetrachloride and may optionally be further purified to remove carbon tetrachloride. This may include further distillation at temperatures of from about 60° C. to about 160° C., and pressures of from about 0.07 atmospheres to about 0.5 atmospheres, to recover carbon tetrachloride and light ends in a light ends stream 82. For example, and as shown in FIG. 2, this partial purification step may take place within a distillation column 80 to produce light ends stream 82, which is rich in carbon tetrachloride, and a bottom ends fraction 84, which is rich in 1,1,1,3,3-pentachloropropane. Light ends stream 82 may also be referred to as overhead fraction 82. Light ends stream 82 may be disposed of as a light ends purge 86. Since light ends stream 82 contains unconverted carbon tetrachloride, it may be recycled back to reactor 50 as a recycle stream 88. When light ends stream 82 is recycled, some light ends may also be purged from light ends purge 86 to control accumulation of unwanted components.

Bottom fraction 84, which can be characterized as a partially purified 1,1,1,3,3-pentachloropropane stream, may then be reactively distilled according to a process of the present invention. The reactive distillation step selectively dehydrochlorinates 1,1,1,3,3-pentachloropropane to make hydrogen chloride (HCl) and 1,1,3,3-tetrachloropropene, where 1,1,3,3-tetrachloropropene and hydrogen chloride can be continuously distilled overhead. For example, partially purified 1,1,1,3,3-pentachloropropane stream 90 may be introduced to reactive distillation column 92 together with ferric chloride 94. Ferric chloride 94 may also be referred to as Lewis acid 94. As suggested above, ferric chloride 94 can be added either dry or as a slurry. As with the previous embodiments, ferric chloride 94 can be added to partially purified 1,1,1,3,3-pentachloropropane stream 90 before stream 90 is introduced to reactive distillation column 92. In other embodiments, ferric chloride 94 can be introduced to partially purified 1,1,1,3,3-pentachloropropane stream 90 within reactive distillation column 92. In one or more embodiments, ferric chloride 94 may be introduced to partially purified 1,1,1,3,3-pentachloropropane stream 90 before stream 90 is introduced to reactive distillation column 92 and directly to reactive distillation column 92. As with the previous embodiments, reactive distillation column 92 may be operated at temperatures from about 60° C. to about 160° C., and pressures of from about 0.05 atmospheres to about 0.5 atmospheres.

In one or more embodiments, an oxidizing agent 85, such as chlorine, is introduced to reactive distillation column 92. This oxidizing agent 85 may be introduced to the feed line introducing the 1,1,1,3,3-pentachloropropane stream 84, or a feed line 87 that directly introduces oxidizing agent 85 to reactive distillation column 92. Oxidizing agent 85 may also be referred to as chlorine 85. In one or more embodiments, oxidizing agent 85 may be introduced to the feed line introducing the 1,1,1,3,3-pentachloropropane stream 84 and to feed line 87 that directly introduces oxidizing agent 85 to reactive distillation column 92.

A volatiles fraction 96, which primarily includes hydrogen chloride, may be collected from distillation column 92 and vented.

The bottom fraction 98 from reactive distillation column 92 can be routed to heavy ends purge 100.

Condensate fraction 102, which is rich in 1,1,3,3-tetrachloropropene, may be further purified by removal of hydrogen chloride within a hydrogen chloride separator 104. In one or more embodiments, hydrogen chloride separator 104 may include a stripping tower. In other embodiments, separator 104 may include a distillation column.

Volatiles fraction 106, which primarily includes hydrogen chloride, may be vented from separator 104. Other light compounds, which have a boiling point below that of the desired 1,1,3,3-tetrachloropropene, may be collected as a distillate fraction, which may be drawn at or near the top section of a distillation tower used as hydrogen chloride separator 104.

The desired 1,1,3,3-tetrachloropropene product 110 may be recovered via a bottom section or a lower side draw 110 of a distillation tower, where a distillation tower is used as separator 104. Where separator 104 is a distillation tower, the distillation may take place at temperatures from about 60° C., to about 160° C., and pressures from about 0.03 atmospheres to about 1.1 atmospheres.

In one or more embodiments, desired 1,1,3,3-tetrachloropropene product 110 can be further purified by using, for example, additional distillation techniques to provide a product of desired purity. For example, distillation tower 112 may be employed. In one or more embodiments, optional purification steps may be used to meet customer specifications.

Process for Producing 1,1,3,3-Tetrachloropropene Using Crude Stream

Figure 3:
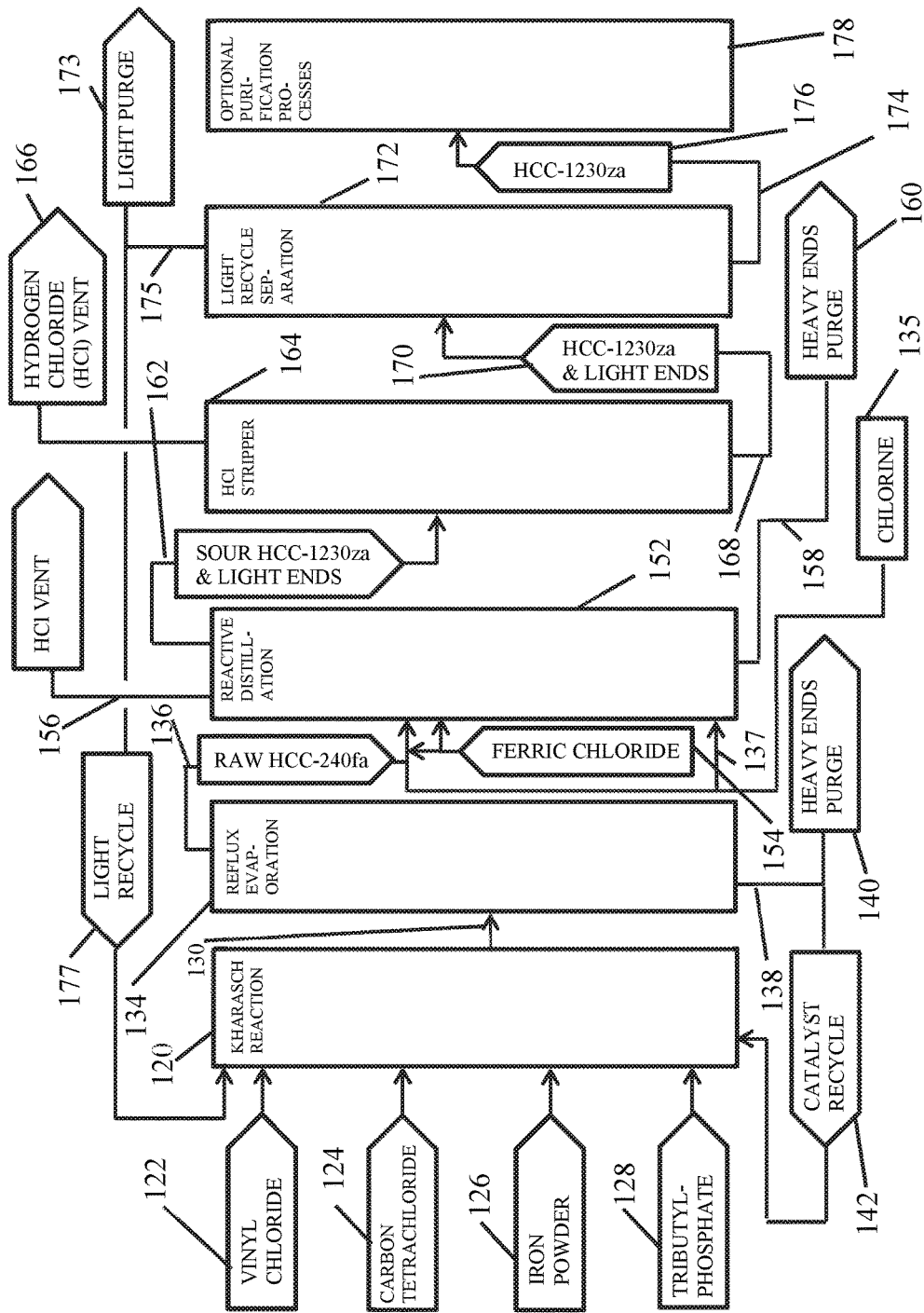
FIG. 3 is a flow chart diagram of a process for producing 1,1,3,3-tetrachloropropene according to embodiments of the invention where a crude stream of 1,1,1,3,3-pentachloropropane is reactively distilled.

An exemplary process for producing 1,1,3,3-tetrachloropropene from a crude 1,1,1,3,3-pentachloropropane stream is shown in FIG. 3. To begin with, 1,1,1,3,3-pentachloropropane is prepared within a reaction vessel 120 by combining vinyl chloride 122, carbon tetrachloride 124, iron powder 126, and an organophosphate (e.g., tributylphosphate) 128. As is generally known in the art, the reaction taking place within a reactor 120, which may be referred to as the Kharasch reaction, takes place at temperatures of from about 80° C. to about 125° C. As suggested above, the Kharasch reaction combines vinyl chloride and carbon tetrachloride (CTC) to make 1,1,1,3,3-pentachloropropane. As is also known in the art, where excess carbon tetrachloride is supplied to reactor 120, reaction selectivity can be improved thereby producing fewer heavy ends.

The raw 1,1,1,3,3-pentachloropropane product stream 130 exits reactor 120 and is delivered to a refluxed evaporator 134, wherein the 1,1,1,3,3-pentachloropropane and light ends are separated as an overhead fraction 136 from the other components, which can include heavy ends and catalyst components. The other components, which have a higher boiling point and include, for example, organophosphates, are separated as a heavy ends fraction 138. In particular embodiments, heavy ends fraction 138 can be routed to a heavy ends purge 140 or, depending on the nature of heavy ends 138, provided as a catalyst recycle stream 142 to reactor 120. In one or more embodiments, reflux evaporator 134 may be operated at temperatures of from about 70° C. to about 120° C., and pressures of from about 0.02 atmospheres to about 0.07 atmospheres.

Overhead fraction 136, which may be referred to as crude 1,1,1,3,3-pentachloropropane product stream 136, raw 1,1,1,3,3-pentachloropropane product stream 136, or distillate stream 136, exits evaporator 134 and is then reactively distilled according to a process of the present invention. The reactive distillation step selectively dehydrochlorinates 1,1,1,3,3-pentachloropropane to make hydrogen chloride (HCl) and 1,1,3,3-tetrachloropropene, where 1,1,3,3-tetrachloropropene and light ends can be continuously distilled overhead. For example, crude 1,1,1,3,3-pentachloropropane stream 136 may be introduced to reactive distillation column 152 together with ferric chloride 154. Ferric chloride 154 may also be referred to as Lewis acid 154. As with the previous embodiments, ferric chloride 154 can be added either dry or as a slurry. As with the previous embodiments, ferric chloride 154 can be added to crude 1,1,1,3,3-pentachloropropane stream 136 before stream 136 is introduced to reactive distillation column 152. In other embodiments, ferric chloride 154 can be introduced to crude 1,1,1,3,3-pentachloropropane stream 136 within reactive distillation column 152. In one or more embodiments, ferric chloride 154 may be introduced to the feed line introducing the 1,1,1,3,3-pentachloropropane stream 136 before stream 136 is introduced to reactive distillation column 152 and directly to reactive distillation column 152. As with the previous embodiments, reactive distillation column 152 may be operated at temperatures from about 60° C. to about 160° C., and pressures of from about 0.05 atmospheres to about 0.5 atmospheres.

In one or more embodiments, an oxidizing agent 135, such as chlorine, is introduced to reactive distillation column 152. Oxidizing agent 135 may also be referred to as chlorine 135. This oxidizing agent 135 may be introduced to the feed line introducing the 1,1,1,3,3-pentachloropropane stream 136, or a feed line 137 that directly introduces oxidizing agent 135 to reactive distillation column 152. In one or more embodiments, oxidizing agent 135 may be introduced to the feed line introducing the 1,1,1,3,3-pentachloropropane stream 136 and directly to reactive distillation column 152 by way of feed line 137.

A volatiles fraction 156, which primarily includes hydrogen chloride, may be collected from reactive distillation column 152 and vented.

The bottom fraction 158 from reactive distillation column 152 can be routed to heavy ends purge 160.

Condensate fraction 162, which is rich in 1,1,3,3-tetrachloropropene, may be further purified by removal of hydrogen chloride within a hydrogen chloride separator 164. In one or more embodiments, hydrogen chloride separator 164 may include a stripping tower. In other embodiments, separator 164 may include a distillation column. Volatiles fraction 166, which primarily includes hydrogen chloride, may be vented from separator 164. The other heavy components, including the desired 1,1,3,3-tetrachloropropene, may be collected as stream 168.

The desired 1,1,3,3-tetrachloropropene product may be recovered via a bottom section or a lower side draw 168 of a distillation tower, where a distillation tower is used as separator 164. Where separator 164 is a distillation tower, the distillation may take place at temperatures from about 60° C., to about 160° C., and pressures from about 0.03 atmospheres to about 1.1 atmospheres.

Stream 168 may be further purified to separate the desired 1,1,3,3-tetrachloropropene product 176 from a light ends stream 175 containing other lightweight, lower boiling materials within stream 168. These lightweight materials may include, for example, unconverted carbon tetrachloride, as well as other chlorinated compounds such as vinyl chloride and the like. This separation may take place within a distillation column 172. Light ends stream 175 may also be referred to as overhead fraction 175. Light ends stream 175 may be disposed of as a light end purge 173. Since light ends stream 175 contains unconverted carbon tetrachloride, it may be recycled back to reactor 120 as a recycle. When light ends stream 175 is recycled, some light ends may also be purged from light ends purge 173 to control accumulation of unwanted components.

The desired product 176 is removed as a heavy ends fraction 174. In one or more embodiments, distillation tower 172 may be operated at temperatures from about 60° C., to about 160° C., and pressures from about 0.05 atmospheres to about 0.5 atmospheres.

In one or more embodiments, desired 1,1,3,3-tetrachloropropene product 176 can be further purified by using, for example, additional distillation techniques to provide a product of desired purity. For example, a distillation tower 178 may be employed. In one or more embodiments, optional purification steps may be used to meet customer specifications.

In order to demonstrate the practice of the present invention, the following examples have been prepared and tested. The examples should not, however, be viewed as limiting the scope of the invention. The claims will serve to define the invention.

EXAMPLES

For the Tables below, as above, HCC-1230za is representative of 1,1,3,3-tetrachloropropene and HCC-240fa is representative of 1,1,1,3,3-pentachloropropane.

The reaction vessel for all examples was a 3-liter Pyrex™ (Corning Incorporated) glass round-bottom flask equipped with a graduated addition funnel and a 20-tray Oldershaw-type vacuum-jacketed Pyrex™ glass distillation column. Atop the column was a reflux head and condenser, with a side draw tube leading to a product receiver. The entire system was connected to a controlled vacuum source. The examples were conducted in a generally semi-batch operation, with discreet weighed overhead samples collected and analyzed by gas chromatography. 1,1,1,3,3-Pentachloropropane was introduced into the bottoms flask periodically via the addition funnel.

Example 1—No Chlorine Addition

In Example 1, the bottoms flask was charged with 0.26 grams anhydrous ferric chloride (FeCl$_3$) and 290.7 grams of 1,1,1,3,3-pentachloropropane. Vacuum and heat were applied until the system began refluxing. Overhead product draw was begun using a 0.7/1 reflux ratio. Over the course of 292 minutes, the overhead temperature gradually increased from 82 to 103 degrees C., while the bottoms rose from 92 to 113 degrees C. Seven timed overhead samples were collected. The cumulative moles of 1,1,3,3-tetrachloropropene recovered and 1,1,1,3,3-pentachloropropane fed at the end of each sample collection period are shown in Table 1 and graphically represented in FIG. 4. The rate of 1,1,3,3-tetrachloropropene formation dropped with time as shown by the decreasing slope of the 1,1,3,3-tetrachloropropene line.

TABLE 1

Example 1 data

| | | | | | | | |
|---|---|---|---|---|---|---|---|
| Cumulative Run Time, min | 24 | 83 | 127 | 177 | 212 | 254 | 292 |
| Overhead Sample Duration, min | 24 | 59 | 44 | 50 | 35 | 42 | 38 |
| Overhead Temp, C. | 82 | 84 | 90 | 89 | 100 | 100 | 103 |
| Bottoms Temp, C. | 92 | 100 | 108 | 111 | 110 | 113 | 113 |
| Absolute Pressure, mm Hg | 98 | 98 | 98 | 98 | 98 | 98 | 98 |
| Overhead Sample, grams | 51 | 147 | 92 | 105 | 83 | 111 | 65 |
| Cumulative grams HCC-240fa Charged | 291 | 485 | 705 | 929 | 929 | 929 | 1059 |
| Incremental grams FeCl3 Charged | 0.26 | 0 | 0 | 0 | 0 | 0 | 0 |
| Cumulative moles HCC-240fa Charged | 1.34 | 2.24 | 3.26 | 4.29 | 4.29 | 4.29 | 4.89 |
| Overhead Sample Comp, wt % | | | | | | | |
| HCC-1230za | 99.2 | 99.1 | 91.7 | 69.2 | 43.1 | 38.8 | 33.7 |
| HCC-240fa | 0.8 | 0.9 | 8.2 | 30.6 | 56.6 | 61.1 | 66.3 |
| Overhead moles | | | | | | | |
| HCC-1230za | 0.282 | 0.807 | 0.469 | 0.406 | 0.198 | 0.239 | 0.122 |
| HCC-240fa | 0.002 | 0.006 | 0.035 | 0.149 | 0.216 | 0.313 | 0.199 |
| Cumulative HCC-1230za | 0.282 | 1.090 | 1.558 | 1.964 | 2.162 | 2.401 | 2.523 |

Example 2—Chlorine Addition

Figure 4:
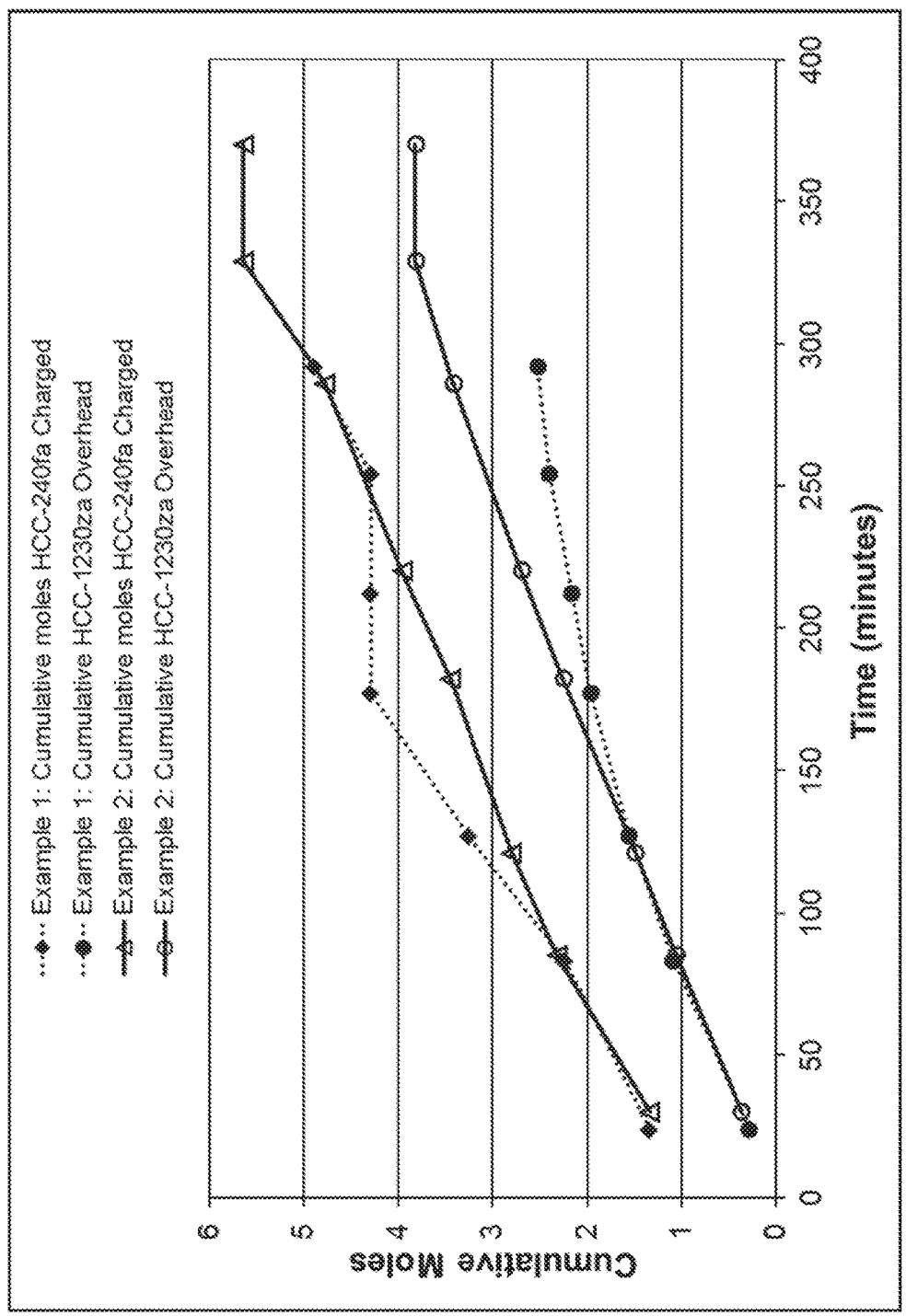
FIG. 4 is a graph showing certain results from Examples 1 and 2.

Example 2 was conducted in the same manner as Example 1, except that 0.21 mole/hr chlorine gas was continuously sparged into the liquid in the bottoms flask. Over 370 minutes, the overhead temperature remained essentially constant between 80 and 85 degrees C. The bottoms temperature rose from 92 to about 100 degrees C. within the first 60 minutes, then stayed there for the duration. Cumulative moles of 1,1,3,3-tetrachloropropene and 1,1,1,3,3-pentachloropropane are also shown in FIG. 4 as a comparison to Example 1. The rate of 1,1,3,3-tetrachloropropene formation stayed essentially constant. The rate after 150 minutes was higher than in Example 1, even though 1,1,1,3,3-pentachloropropane was introduced at a similar rate.

along with each mole of 1,1,1,3,3-pentachloropropane added to the bottoms flask. No chlorine was fed. Thus, 459.6 grams of 1,1,1,3,3-pentachloropropane and 0.53 grams of $FeCl_3$ were charged to the flask initially. The mixture was boiled and 1,1,3,3-tetrachloropropene product was removed from the column overhead as before. The first overhead sample, 160.4 grams, was collected for 63 minutes. A mixture of 0.26 grams of $FeCl_3$ in 222.7 grams of 1,1,1,3,3-pentachloropropane was slowly added to the bottoms flask as the next overhead sample was collected. Similar additions were conducted for the next three overhead samples. Over 402 minutes, overhead temperatures remained constant between 83 and 85 degrees C. Bottoms temperature slowly

TABLE 2

Example 2 data

| | | | | | | | | |
|---|---|---|---|---|---|---|---|---|
| Cumulative Run Time, min | 30 | 85 | 121 | 182 | 220 | 286 | 329 | 370 |
| Overhead Sample Duration, min | 30 | 55 | 36 | 61 | 38 | 66 | 43 | 41 |
| Overhead Temp, C. | 85 | 81 | 81 | 83 | 82 | 82 | 80 | 83 |
| Bottoms Temp, C. | 92 | 98 | 99 | 100 | 101 | 102 | 101 | 101 |
| Absolute Pressure, mm Hg | 98 | 100 | 98 | 100 | 100 | 100 | 98 | 98 |
| Overhead Sample grams | 68 | 127 | 80 | 142 | 82 | 140 | 77 | 139 |
| Cumulative grams HCC-240fa Charged | 291 | 502 | 605 | 746 | 857 | 1034 | 1221 | 1221 |
| Incremental grams FeCl3 Charged | 0.27 | 0 | 0 | 0 | 0 | 0 | 0 | 0 |
| Cumulative moles HCC-240fa Charged | 1.34 | 2.32 | 2.80 | 3.45 | 3.96 | 4.78 | 5.64 | 5.64 |
| Overhead Sample Comp, wt % | | | | | | | | |
| HCC-1230za | 98.8 | 97.0 | 97.7 | 96.5 | 96.9 | 93.5 | 93.9 | 93.0 |
| HCC-240fa | 1.2 | 3.0 | 2.3 | 3.5 | 3.0 | 6.5 | 5.8 | 6.9 |
| Overhead moles | | | | | | | | |
| HCC-1230za | 0.371 | 0.687 | 0.433 | 0.764 | 0.442 | 0.727 | 0.400 | 0.00 |
| HCC-240fa | 0.004 | 0.017 | 0.009 | 0.023 | 0.012 | 0.042 | 0.021 | 0.00 |
| Cumulative HCC-1230za | 0.371 | 1.058 | 1.491 | 2.255 | 2.697 | 3.424 | 3.824 | 3.824 |

Example 3—No Chlorine Addition, Periodic $FeCl_3$ Addition

Figure 5:
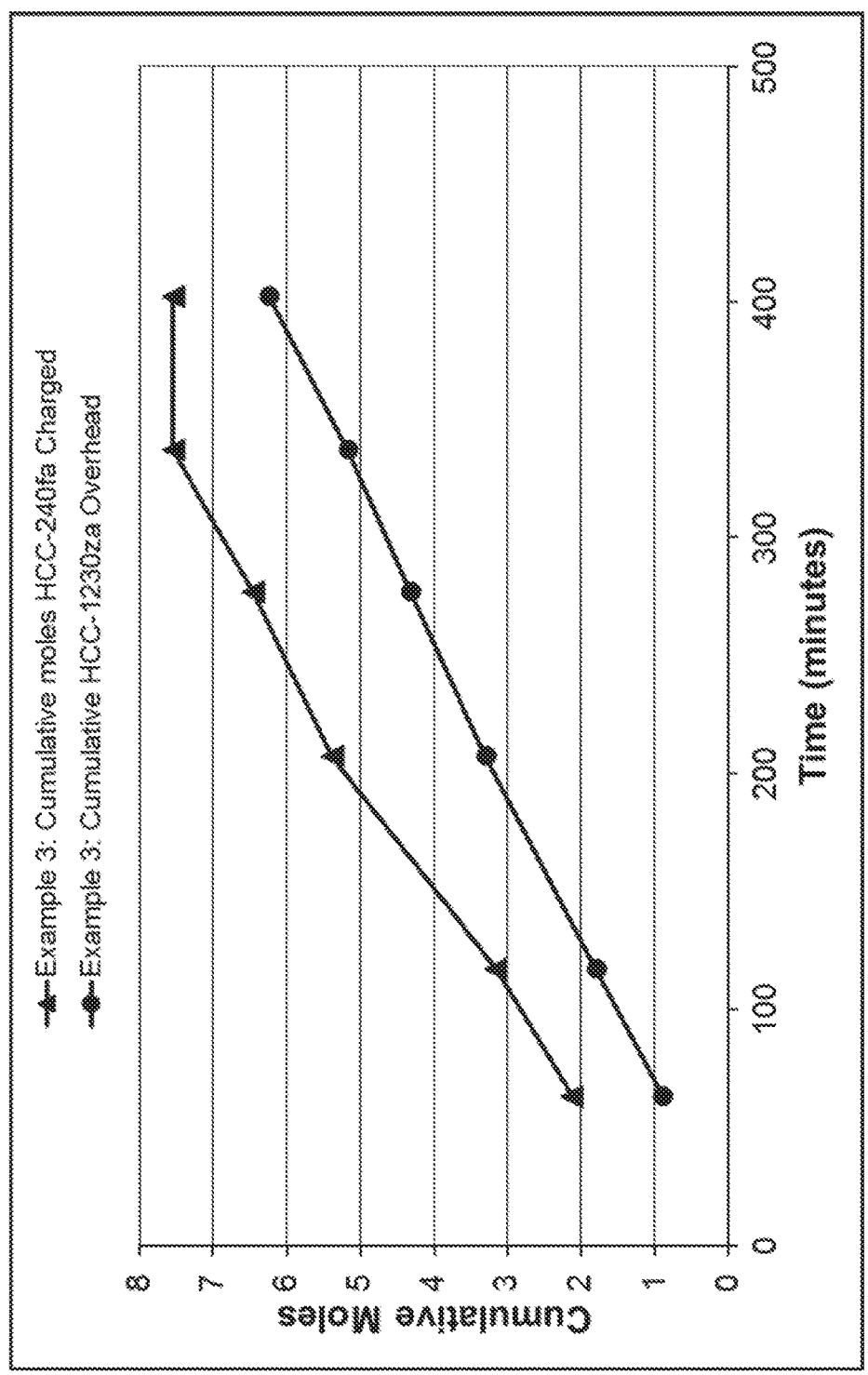
FIG. 5 is a graph showing certain results from Example 3.

This example was conducted similarly to Example 1, except that 0.25 gram of anhydrous $FeCl_3$ was introduced rose from 92 to 98 degrees. Cumulative moles of 1,1,3,3-tetrachloropropene and 1,1,1,3,3-pentachloropropane are shown in Table 3 and in FIG. 5. Again, the rate of 1,1,3,3-tetrachloropropene formation remained much higher with time than in Example 1 with only the initial charge of $FeCl_3$.

TABLE 3

| Example 3 data | | | | | | |
|---|---|---|---|---|---|---|
| Cumulative Run Time, min | 63 | 117 | 207 | 277 | 337 | 402 |
| Overhead Sample Duration, min | 63 | 54 | 90 | 70 | 60 | 65 |
| Overhead Temp, C. | 84 | 83 | 85 | 84 | 83 | 85 |
| Bottoms Temp, C. | 92 | 93 | 95 | 96 | 97 | 98 |
| Absolute Pressure, mm Hg | 103 | 100 | 98 | 100 | 98 | 98 |
| Overhead Sample grams | 160 | 163 | 270 | 187 | 152 | 192 |
| Cumulative grams HCC-240fa Charged | 460 | 682 | 1164 | 1396 | 1633 | 1633 |
| Incremental grams FeCl3 Charged | 0.53 | 0.26 | 0.63 | 0.29 | 0.32 | 0 |
| Cumulative moles HCC-240fa Charged | 2.12 | 3.15 | 5.38 | 6.46 | 7.55 | 7.55 |
| Overhead Sample Comp, wt % | | | | | | |
| HCC-1230za | 100 | 99.9 | 99.9 | 99.7 | 99.6 | 99.9 |
| HCC-240fa | 0.1 | 0.1 | 0.1 | 0.3 | 0.4 | 0.1 |
| Overhead moles | | | | | | |
| HCC-1230za | 0.891 | 0.904 | 1.496 | 1.033 | 0.843 | 1.067 |
| HCC-240fa | 0.000 | 0.001 | 0.001 | 0.003 | 0.003 | 0.001 |
| Cumulative HCC-1230za | 0.891 | 1.796 | 3.292 | 4.326 | 5.168 | 6.235 |

Example 4—Chlorine Addition, No FeCl₃ Present

The catalytic effect of chlorine alone was tested in Example 4. Thus, 373 grams of 1,1,1,3,3-pentachloropropane with no FeCl$_3$ were charged to the flask. The mixture was boiled and overhead product removed as before. Three overhead samples were collected over an 85 minute total run time. One addition of 1,1,1,3,3-pentachloropropane was made after the second overhead sample. Only 0.03 moles of 1,1,3,3-tetrachloropropene were formed after 85 minutes, compared to 1-2 moles at similar times in examples 1-3, indicating the catalytic effect of FeCl$_3$.

TABLE 4

| Example 4 data | | | |
|---|---|---|---|
| Cumulative Run Time, min | 25 | 55 | 85 |
| Overhead Sample Duration, min | 25 | 30 | 30 |
| Overhead Temp, C. | 116 | 114 | 115 |
| Bottoms Temp, C. | 120 | 119 | 119 |
| Absolute Pressure, mmHg | 108 | 103 | 103 |
| Overhead Sample grams | 35 | 60 | 47 |
| Cumulative grams HCC-240fa Charged | 373 | 373 | 455 |
| Incremental grams FeCl3 Charged | 0 | 0 | 0 |
| Cumulative moles HCC-240fa Charged | 1.72 | 1.72 | 2.10 |
| Overhead Sample Comp, wt % | | | |
| HCC-1230za | 14.4 | 0.5 | 0.2 |
| HCC-240fa | 85.6 | 99.5 | 99.8 |
| Overhead moles | | | |
| HCC-1230za | 0.028 | 0.002 | 0.000 |
| HCC-240fa | 0.139 | 0.274 | 0.217 |
| Cumulative HCC-1230za | 0.028 | 0.030 | 0.030 |

Various modifications and alterations that do not depart from the scope and spirit of this invention will become apparent to those skilled in the art. This invention is not to be duly limited to the illustrative embodiments set forth herein.

What is claimed is:

1. A process for the manufacture of 1,1,3,3-tetrachloropropene, the process comprising:
    combining carbon tetrachloride, vinyl chloride, an organophosphate compound, iron metal, and ferric chloride under conditions sufficient to react the carbon tetrachloride and the vinyl chloride to produce 1,1,1,3,3-pentachloropropane within a reaction stream,
    separating the reaction stream into a high-boiling-point-component stream and a distillate fraction, the distillate fraction including the 1,1,1,3,3-pentachloropropane, and
    introducing the distillate fraction to a reactive distillation column, thereby dehydrochlorinating the 1,1,1,3,3-pentachloropropane.

2. The process of claim 1, where said step of separating takes place at a temperature from about 70° C. to about 120° C.

3. The process of claim 1, where said step of separating takes place at a pressure of at least 0.020 atmospheres.

4. The process of claim 1, where the distillate fraction further includes isomers of 1,1,1,3,3-pentachloropropane, unconverted vinyl chloride, unconverted carbon tetrachloride, and other light byproducts.

5. The process of claim 1, further comprising a step of introducing additional ferric chloride to the reactive distillation column.

6. The process of claim 1, further comprising a step of introducing an oxidizing agent to the reactive distillation column.

7. The process of claim 1, where the reactive distillation column is at a pressure of from about 0.05 atmospheres to about 0.5 atmospheres.

8. The process of claim 1, where the reactive distillation column is at a temperature of from about 60° C. to about 160° C.

9. The process of claim 4, further comprising a step of introducing additional ferric chloride to the reactive distillation column.

10. The process of claim 9, where the additional ferric chloride is introduced to the distillate fraction prior to said step of introducing the distillate fraction to the reactive distillation column.

11. The process of claim 9, where the additional ferric chloride is introduced directly to the reactive distillation column separately from the distillate fraction.

12. The process of claim 1, where the organophosphate compound is tributylphosphate.

13. A process for the manufacture of 1,1,3,3-tetrachloropropene, the process comprising:
    combining carbon tetrachloride, vinyl chloride, an organophosphate compound, iron metal, and ferric chloride, to produce a product stream including 1,1,1,3,3-pentachloropropane and organophosphates, separating the 1,1,1,3,3-pentachloropropane from the product stream to form a first stream, separating the organophosphates from the product stream to form a second stream, and reactively distilling the first stream containing the 1,1,1,3,3-pentachloropropane, to thereby dehydrochlorinate the 1,1,1,3,3-pentachloropropane.

* * * * *